United States Patent
Wright et al.

(10) Patent No.: US 10,392,632 B2
(45) Date of Patent: Aug. 27, 2019

(54) AAV8 VECTOR WITH ENHANCED FUNCTIONAL ACTIVITY AND METHODS OF USE THEREOF

(75) Inventors: John Fraser Wright, Princeton, NJ (US); Olga Zelenaia, Ardmore, PA (US); Bernd Hauck, Hamilton, NJ (US); Federico Mingozzi, Paris (FR); Katherine A. High, Merion Station, PA (US)

(73) Assignee: THE CHILDREN'S HOSPITAL OF PHILADELPHIA, Philadelphia, PA (US)

( * ) Notice: Subject to any disclaimer, the term of this patent is extended or adjusted under 35 U.S.C. 154(b) by 0 days.

(21) Appl. No.: 13/985,351

(22) PCT Filed: Feb. 14, 2012

(86) PCT No.: PCT/US2012/025088
§ 371 (c)(1),
(2), (4) Date: Oct. 21, 2013

(87) PCT Pub. No.: WO2012/112578
PCT Pub. Date: Aug. 23, 2012

(65) Prior Publication Data
US 2014/0037585 A1 Feb. 6, 2014

Related U.S. Application Data

(60) Provisional application No. 61/442,606, filed on Feb. 14, 2011.

(51) Int. Cl.
| | |
|---|---|
| *C12N 15/63* | (2006.01) |
| *C12N 15/86* | (2006.01) |
| *A61K 38/48* | (2006.01) |
| *A61K 48/00* | (2006.01) |
| *C07K 14/005* | (2006.01) |

(52) U.S. Cl.
CPC .......... *C12N 15/86* (2013.01); *A61K 38/4846* (2013.01); *A61K 48/0008* (2013.01); *C07K 14/005* (2013.01); *C12N 2710/14122* (2013.01); *C12N 2750/14143* (2013.01)

(58) Field of Classification Search
CPC .............. C07K 14/005; A61K 48/0008; A61K 38/4846; C12N 15/86; C12N 2710/14122; C12N 2750/14143
USPC ........................................................ 424/93.1
See application file for complete search history.

(56) References Cited

U.S. PATENT DOCUMENTS

2003/0053990 A1 3/2003 Rabinowitz et al.
2003/0228282 A1 12/2003 Gao et al.

OTHER PUBLICATIONS

Vandenberghe et al 2009, Gene therapy 16:311-319.*
USPTO (STIC) Sequence Search Jul. 13, 2015:pp. 1-3.*
Son, G.H. etal. "Excision of the First Intron from the Gonadotropin-releasing Hormone (GnRH) Transcript Serves as a Key Regulatory Step for GnRH Biosynthesis" The Journal of Biological Chemistry, May 16, 2003, pp. 18037-18044, vol. 278, No. 2.*
Kamhi, E. et al. "AUG sequences are required to sustain nonsense-codon-mediated suppression of splicing" Nucleic Acids Research, Jul. 19, 2006, pp. 3421-3433, vol. 34.*
Fath et al Multiparameter RNA and Codon Optimization: A Standardized Tool to Assess and Enhance Autologous Mammalian Gene Expression PLOS one Mar. 2011 | vol. 6 | Issue 3 | e17596 pp. 1-13.*
Becerra, S.P., et al. "Direct mapping of adeno-associated virus capsid proteins B and C: a possible ACG initiation codon." Proc Natl Acad Sci U S A. Dec. 1985;82(23):7919-23.
Gao, G.P., et al. "Novel adeno-associated viruses from rhesus monkeys as vectors for human gene therapy." Proc Natl Acad Sci U S A. Sep. 3, 2002;99(18):11854-9. Epub Aug. 21, 2002.
Wu, P., et al. "Mutational analysis of the adeno-associated virus type 2 (AAV2) capsid gene and construction of AAV2 vectors with altered tropism." J Virol. Sep. 2000;74(18):8635-47.
Hauck, B., et al., Generation and Characterization of Chimeric Recombinant AAV Vectors, Molecular Therapy, 2003, 7(3):419-425.
Yang, Q., et al., Development of Novel Cell Surface CD34-Targeted Recombinant Adenoassociated Virus Vecors for Gene Therapy, Human Gene Therapy, 1998, 9:1929-1937.
Zelenaia, O., et al., A Capsid Composition Variant Containing Four VP Proteins Caused b a Novel Start Codon at Position 219 of the Nucleotide Sequence of AAV8 Cap, Abstract #403, Molecular Therapy, 2011, 19(Supp. 1):S156.
European Application No. 12746664.7, Supplementary European Search Report dated Mar. 11, 2015.

* cited by examiner

*Primary Examiner* — Maria G Leavitt
(74) *Attorney, Agent, or Firm* — Pillsbury Winthrop Shaw Pittman LLP; Robert M. Bedgood

(57) ABSTRACT

This application relates to the fields of gene therapy and molecular biology. In accordance with the present invention, an adeno-associated virus (AAV) vector comprising an altered capsid protein is provided. More specifically, this invention provides adeno-associated viral vectors comprising protein capsid variants which accelerate vector breakdown and clearance, thereby reducing undesirable immune responses.

22 Claims, 7 Drawing Sheets
Specification includes a Sequence Listing.

AAV8 Cap (Gene bank AF513852.1) versus pAAB8PK plasmid complete sequence

```
                                            2375                                              2424
             AAV8-cap      (1)    ----------ATGGCTGCCGATGGTTATCTTCCAGATTGGCTCGAGGACA
pAAV8PK SeqWright Jul 08  (2375)  TAAATCAGGTATGGCTGCCGATGGTTATCTTCCAGATTGGCTCGAGGACA
                                            2425                                              2474
             AAV8-cap     (41)    ACCTCTCTGAGGGCATTCGCGAGTGGTGGGCGCTGAAACCTGGAGCCCCG
pAAV8PK SeqWright Jul 08  (2425)  ACCTCTCTGAGGGCATTCGCGAGTGGTGGGCGCTGAAACCTGGAGCCCCG
                                            2475                                              2524
             AAV8-cap     (91)    AAGCCCAAAGCCAACCAGCAAAAGCAGGACGACGGCCGGGTCTGGTGCT
pAAV8PK SeqWright Jul 08  (2475)  AAGCCCAAAGCCAACCAGCAAAAGCAGGACGACGGCCGGGTCTGGTGCT
                                            2525                                              2574
             AAV8-cap    (141)    TCCTGGCTACAAGTACCTCGGACCCTTCAACGGACTCGACAAGGGGAGC
pAAV8PK SeqWright Jul 08  (2525)  TCCTGGCTACAAGTACCTCGGACCCTTCAACGGACTCGACAAGGGGAGC
                                            2575                                              2624
             AAV8-cap    (191)    CCGTCAACGCGGCGGACGCAGCGGCCCTGGAGCACGACAAGGCCTACGAC
pAAV8PK SeqWright Jul 08  (2575)  CCGTCAACGCGGCGGACGCAGCGGCCCTGGAGCACGACAAGGCCTACGAC
                                            2625                                              2674
             AAV8-cap    (241)    CAGCAGCTGCAGGCGGGTGACAATCCGTACCTGCGGTATAACCACGCCGA
pAAV8PK SeqWright Jul 08  (2625)  CAGCAGCTGCAGGCGGGTGACAATCCGTACCTGCGGTATAACCACGCCGA
                                            2675                                              2724
             AAV8-cap    (291)    CGCCGAGTTTCAGGAGCGTCTGCAAGAAGATACGTCTTTTGGGGGCAACC
pAAV8PK SeqWright Jul 08  (2675)  CGCCGAGTTTCAGGAGCGTCTGCAAGAAGATACGTCTTTTGGGGGCAACC
                                            2725                                              2774
             AAV8-cap    (341)    TCGGGCGAGCAGTCTTCCAGGCCAAGAAGCGGGTTCTCGAACCTCTCGGT
pAAV8PK SeqWright Jul 08  (2725)  TCGGGCGAGCAGTCTTCCAGGCCAAGAAGCGGGTTCTCGAACCTCTCGGT
                                            2775                                              2824
             AAV8-cap    (391)    CTGGTTGAGGAAGGCGCTAAGACGGCTCCTGGAAAGAAGAGACCGGTAGA
pAAV8PK SeqWright Jul 08  (2775)  CTGGTTGAGGAAGGCGCTAAGACGGCTCCTGGAAAGAAGAGACCGGTAGA
                                            2825                                              2874
             AAV8-cap    (441)    GCCATCACCCCAGCGTTCTCCAGACTCCTCTACGGGCATCGGCAAGAAAG
pAAV8PK SeqWright Jul 08  (2825)  GCCATCACCCCAGCGTTCTCCAGACTCCTCTACGGGCATCGGCAAGAAAG
                                            2875                                              2924
             AAV8-cap    (491)    GCCAACAGCCCGCCAGAAAAAGACTCAATTTTGGTCAGACTGGCGACTCA
```

Figure 2

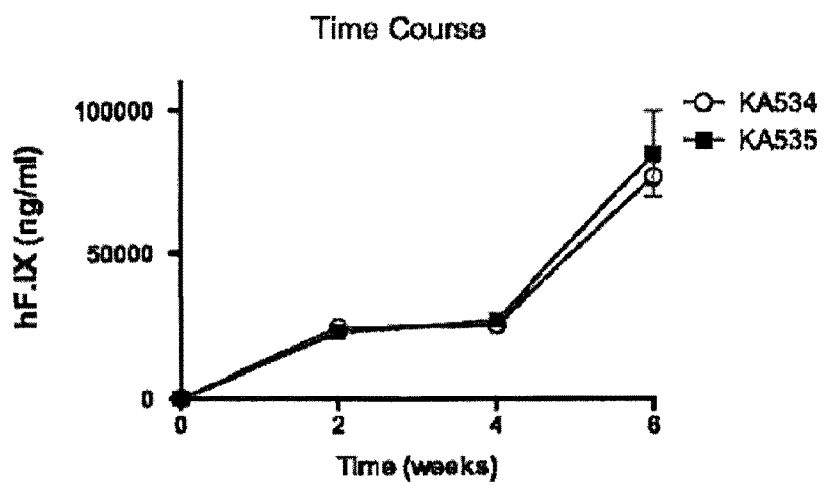
A
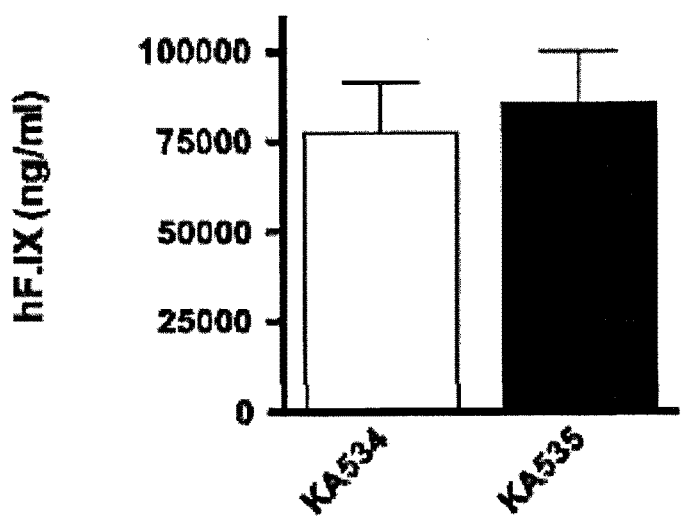
Figure 4

Sequence of AAV8 VP1.5: Panel A (Assuming Leucine at position 1)

```
1
LEHDKAYDQQ LQAGDNPYLR YNHADAEFQE RLQEDTSFGG NLGRAVFQAK
51
KRVLEPLGLV EEGAKTAPGK KRPVEPSPQR SPDSSTGIGK KGQQPARKRL
101
NFGQTGDSES VPDPQPLGEP PAAPSGVGPN TMAAGGGAPM ADNNEGADGV
151
GSSSGNWHCD STWLGDRVIT TSTRTWALPT YNNHLYKQIS NGTSGGATND
201
NTYFGYSTPW GYFDFNRFHC HFSPRDWQRL INNNWGFRPK RLSFKLFNIQ
251
VKEVTQNEGT KTIANNLTST IQVFTDSEYQ LPYVLGSAHQ GCLPPFPADV
301
FMIPQYGYLT LNNGSQAVGR SSFYCLEYFP SQMLRTGNNF QFTYTFEDVP
351
FHSSYAHSQS LDRLMNPLID QYLYYLSRTQ TTGGTANTQT LGFSQGGPNT
401
MANQAKNWLP GPCYRQQRVS TTTGQNNNSN FAWTAGTKYH LNGRNSLANP
451
GIAMATHKDD EERFFPSNGI LIFGKQNAAR DNADYSDVML TSEEEIKTTN
501
PVATEEYGIV ADNLQQQNTA PQIGTVNSQG ALPGMVWQNR DVYLQGPIWA
551
KIPHTDGNFH PSPLMGGFGL KHPPPQILIK NTPVPADPPT TFNQSKLNSF
601
ITQYSTGQVS VEIEWELQKE NSKRWNPEIQ YTSNYYKSTS VDFAVNTEGV
651
YSEPRPIGTR YLTRNL
```

Sequence of AAV8 VP1.5: Panel B (Assuming Methionine at position 1)

```
1
MEHDKAYDQQ LQAGDNPYLR YNHADAEFQE RLQEDTSFGG NLGRAVFQAK
51
KRVLEPLGLV EEGAKTAPGK KRPVEPSPQR SPDSSTGIGK KGQQPARKRL
101
NFGQTGDSES VPDPQPLGEP PAAPSGVGPN TMAAGGGAPM ADNNEGADGV
151
GSSSGNWHCD STWLGDRVIT TSTRTWALPT YNNHLYKQIS NGTSGGATND
201
NTYFGYSTPW GYFDFNRFHC HFSPRDWQRL INNNWGFRPK RLSFKLFNIQ
251
VKEVTQNEGT KTIANNLTST IQVFTDSEYQ LPYVLGSAHQ GCLPPFPADV
301
FMIPQYGYLT LNNGSQAVGR SSFYCLEYFP SQMLRTGNNF QFTYTFEDVP
351
FHSSYAHSQS LDRLMNPLID QYLYYLSRTQ TTGGTANTQT LGFSQGGPNT
401
MANQAKNWLP GPCYRQQRVS TTTGQNNNSN FAWTAGTKYH LNGRNSLANP
451
GIAMATHKDD EERFFPSNGI LIFGKQNAAR DNADYSDVML TSEEEIKTTN
501
PVATEEYGIV ADNLQQQNTA PQIGTVNSQG ALPGMVWQNR DVYLQGPIWA
551
KIPHTDGNFH PSPLMGGFGL KHPPPQILIK NTPVPADPPT TFNQSKLNSF
601
ITQYSTGQVS VEIEWELQKE NSKRWNPEIQ YTSNYYKSTS VDFAVNTEGV
651
YSEPRPIGTR YLTRNL
```

Figure 5

```
                              (208) 208        220       230       240       250       260        278
AAV8 Cap GeneBank AF513852 (208) GCAGCGGCCCTCGAGCACGACAAGGCCTACGACCAGCAGCTGCAGGCGGGTGACAATCCGTACCTGCGG
                  AAV1 Cap (208) GCAGCGGCCCTCGAGCACGACAAGGCCTACGACCAGCAGCTCAAAGCGGGTGACAATCCGTACCTTCGG
                  AAV6 Cap (208) GCAGCGGCCCTCGAGCACGACAAGGCCTACGACCAGCAGCTCAAAGCGGGTGACAATCCGTACCTGCGG
                  AAV9 Cap (208) GCGGCGGCCCTCGAGCACGACAAGGCCTACGACCAGCAGCTCAAGGCCGGAGACAACCCGTACCTCAAG
```

Figure 6

AAV8 Cap (Gene bank AF513852.1) versus pAAB8PK plasmid complete sequence

```
                                        2375                                              2424
            AAV8-cap     (1)    ----------ATGGCTGCCGATGGTTATCTTCCAGATTGGCTCGAGGACA
pAAV8PK SeqWright Jul 08 (2375) TAAATCAGGTATGGCTGCCGATGGTTATCTTCCAGATTGGCTCGAGGACA
                                2425                                              2474
            AAV8-cap     (41)   ACCTCTCTGAGGGCATTCGCGAGTGGTGGGCGCTGAAACCTGGAGCCCCG
pAAV8PK SeqWright Jul 08 (2425) ACCTCTCTGAGGGCATTCGCGAGTGGTGGGCGCTGAAACCTGGAGCCCCG
                                2475                                              2524
            AAV8-cap     (91)   AAGCCCAAAGCCAACCAGCAAAAGCAGGACGACGGCCGGGGTCTGGTGCT
pAAV8PK SeqWright Jul 08 (2475) AAGCCCAAAGCCAACCAGCAAAAGCAGGACGACGGCCGGGGTCTGGTGCT
                                2525                                              2574
            AAV8-cap     (141)  TCCTGGCTACAAGTACCTCGGACCCTTCAACGGACTCGACAAGGGGGAGC
pAAV8PK SeqWright Jul 08 (2525) TCCTGGCTACAAGTACCTCGGACCCTTCAACGGACTCGACAAGGGGGAGC
                                2575                                              2624
            AAV8-cap     (191)  CCGTCAACGCGGCGGACGCAGCGGCCCTGGAGCACGACAAGGCCTACGAC
pAAV8PK SeqWright Jul 08 (2575) CCGTCAACGCGGCGGACGCAGCGGCCCTGGAGCACGACAAGGCCTACGAC
                                2625                                              2674
            AAV8-cap     (241)  CAGCAGCTGCAGGCGGGTGACAATCCGTACCTGCGGTATAACCACGCCGA
pAAV8PK SeqWright Jul 08 (2625) CAGCAGCTGCAGGCGGGTGACAATCCGTACCTGCGGTATAACCACGCCGA
                                2675                                              2724
            AAV8-cap     (291)  CGCCGAGTTTCAGGAGCGTCTGCAAGAAGATACGTCTTTTGGGGGCAACC
pAAV8PK SeqWright Jul 08 (2675) CGCCGAGTTTCAGGAGCGTCTGCAAGAAGATACGTCTTTTGGGGGCAACC
                                2725                                              2774
            AAV8-cap     (341)  TCGGGCGAGCAGTCTTCCAGGCCAAGAAGCGGGTTCTCGAACCTCTCGGT
pAAV8PK SeqWright Jul 08 (2725) TCGGGCGAGCAGTCTTCCAGGCCAAGAAGCGGGTTCTCGAACCTCTCGGT
                                2775                                              2824
            AAV8-cap     (391)  CTGGTTGAGGAAGGCGCTAAGACGGCTCCTGGAAAGAAGAGACCGGTAGA
pAAV8PK SeqWright Jul 08 (2775) CTGGTTGAGGAAGGCGCTAAGACGGCTCCTGGAAAGAAGAGACCGGTAGA
                                2825                                              2874
            AAV8-cap     (441)  GCCATCACCCCAGCGTTCTCCAGACTCCTCTACGGGCATCGGCAAGAAAG
pAAV8PK SeqWright Jul 08 (2825) GCCATCACCCCAGCGTTCTCCAGACTCCTCTACGGGCATCGGCAAGAAAG
                                2875                                              2924
            AAV8-cap     (491)  GCCAACAGCCCGCCAGAAAAAGACTCAATTTTGGTCAGACTGGCGACTCA
```

Figure 7

```
                              SEQUENCE LISTING

<160> NUMBER OF SEQ ID NOS: 9

<210> SEQ ID NO 1
<211> LENGTH: 540
<212> TYPE: DNA
<213> ORGANISM: Adeno-associated virus - 8

<400> SEQUENCE: 1
atggctgccg atggttatct tccagattgg ctcgaggaca acctctctga gggcattcgc      60
gagtggtggg cgctgaaacc tggagccccg aagcccaaag ccaaccagca aaagcaggac     120
gacggccggg gtctggtgct tcctggctac aagtacctcg gacccttcaa cggactcgac     180 aaggggagc ccgtcaacgc ggcggacgca gcggccctcg agcacgacaa ggcctacgac     240
cagcagctgc aggcgggtga caatccgtac ctgcggtata accacgccga cgccgagttt     300
caggagcgtc tgcaagaaga tacgtctttt ggggggcaacc tcgggcgagc agtcttccag     360
gccaagaagc gggttctcga acctctcggt ctggttgagg aaggcgctaa gacggctcct     420
ggaaagaaga gaccggtaga gccatcaccc cagcgttctc cagactcctc tacgggcatc     480
ggcaagaaag ccaacagcc cgccagaaaa agactcaatt ttggtcagac tggcgactca     540

<210> SEQ ID NO 2
<211> LENGTH: 500
<212> TYPE: DNA
<213> ORGANISM: Adeno-associated virus - 8

<400> SEQUENCE: 2
taaatcaggt atggctgccg atggttatct tccagattgg ctcgaggaca acctctctga      60
gggcattcgc gagtggtggg cgctgaaacc tggagccccg aagcccaaag ccaaccagca     120
aaagcaggac gacggccggg gtctggtgct tcctggctac aagtacctcg gacccttcaa     180
cggactcgac aaggggagc ccgtcaacgc ggcggacgca gcggccctgg agcacgacaa     240
ggcctacgac cagcagctgc aggcgggtga caatccgtac ctgcggtata accacgccga     300
cgccgagttt caggagcgtc tgcaagaaga tacgtctttt ggggggcaacc tcgggcgagc     360 agtcttccag gccaagaagc gggttctcga acctctcggt ctggttgagg aaggcgctaa     420
gacggctcct ggaaagaaga gaccggtaga gccatcaccc cagcgttctc cagactcctc     480
tacgggcatc ggcaagaaag                                                  500

<210> SEQ ID NO 3
<211> LENGTH: 666
<212> TYPE: PRT
<213> ORGANISM: Adeno-associated virus - 8

<400> SEQUENCE: 3

Leu Glu His Asp Lys Ala Tyr Asp Gln Gln Leu Gln Ala Gly Asp Asn
 1               5                  10                  15

Pro Tyr Leu Arg Tyr Asn His Ala Asp Ala Glu Phe Gln Glu Arg Leu
            20                  25                  30

Gln Glu Asp Thr Ser Phe Gly Gly Asn Leu Gly Arg Ala Val Phe Gln
        35                  40                  45

Ala Lys Lys Arg Val Leu Glu Pro Leu Gly Leu Val Glu Glu Gly Ala
    50                  55                  60
```

-continued

Lys Thr Ala Pro Gly Lys Arg Pro Val Glu Pro Ser Pro Gln Arg
65                  70                  75                  80

Ser Pro Asp Ser Ser Thr Gly Ile Gly Lys Lys Gly Gln Gln Pro Ala
            85                  90                  95

Arg Lys Arg Leu Asn Phe Gly Gln Thr Gly Asp Ser Glu Ser Val Pro
            100                 105                 110

Asp Pro Gln Pro Leu Gly Glu Pro Pro Ala Ala Pro Ser Gly Val Gly
            115                 120                 125

Pro Asn Thr Met Ala Ala Gly Gly Ala Pro Met Ala Asp Asn Asn
130                 135                 140

Glu Gly Ala Asp Gly Val Gly Ser Ser Gly Asn Trp His Cys Asp
145                 150                 155                 160

Ser Thr Trp Leu Gly Asp Arg Val Ile Thr Thr Ser Thr Arg Thr Trp
                165                 170                 175

Ala Leu Pro Thr Tyr Asn Asn His Leu Tyr Lys Gln Ile Ser Asn Gly
                180                 185                 190

Thr Ser Gly Gly Ala Thr Asn Asp Asn Thr Tyr Phe Gly Tyr Ser Thr
            195                 200                 205

Pro Trp Gly Tyr Phe Asp Phe Asn Arg Phe His Cys His Phe Ser Pro
210                 215                 220

Arg Asp Trp Gln Arg Leu Ile Asn Asn Asn Trp Gly Phe Arg Pro Lys
225                 230                 235                 240

Arg Leu Ser Phe Lys Leu Phe Asn Ile Gln Val Lys Glu Val Thr Gln
                245                 250                 255

Asn Glu Gly Thr Lys Thr Ile Ala Asn Asn Leu Thr Ser Thr Ile Gln
            260                 265                 270

Val Phe Thr Asp Ser Glu Tyr Gln Leu Pro Tyr Val Leu Gly Ser Ala
                275                 280                 285

His Gln Gly Cys Leu Pro Pro Phe Pro Ala Asp Val Phe Met Ile Pro
    290                 295                 300

Gln Tyr Gly Tyr Leu Thr Leu Asn Asn Gly Ser Gln Ala Val Gly Arg
305                 310                 315                 320

Ser Ser Phe Tyr Cys Leu Glu Tyr Phe Pro Ser Gln Met Leu Arg Thr
                325                 330                 335

Gly Asn Asn Phe Gln Phe Thr Tyr Thr Phe Glu Asp Val Pro Phe His
            340                 345                 350

Ser Ser Tyr Ala His Ser Gln Ser Leu Asp Arg Leu Met Asn Pro Leu
            355                 360                 365

Ile Asp Gln Tyr Leu Tyr Tyr Leu Ser Arg Thr Gln Thr Thr Gly Gly
370                 375                 380

Thr Ala Asn Thr Gln Thr Leu Gly Phe Ser Gln Gly Gly Pro Asn Thr
385                 390                 395                 400

Met Ala Asn Gln Ala Lys Asn Trp Leu Pro Gly Pro Cys Tyr Arg Gln
                405                 410                 415

Gln Arg Val Ser Thr Thr Thr Gly Gln Asn Asn Asn Ser Asn Phe Ala
            420                 425                 430

Trp Thr Ala Gly Thr Lys Tyr His Leu Asn Gly Arg Asn Ser Leu Ala
            435                 440                 445

Asn Pro Gly Ile Ala Met Ala Thr His Lys Asp Asp Glu Glu Arg Phe
450                 455                 460

Phe Pro Ser Asn Gly Ile Leu Ile Phe Gly Lys Gln Asn Ala Ala Arg
465                 470                 475                 480

Asp Asn Ala Asp Tyr Ser Asp Val Met Leu Thr Ser Glu Glu Ile
            485                 490                 495

Lys Thr Thr Asn Pro Val Ala Thr Glu Glu Tyr Gly Ile Val Ala Asp
            500                 505                 510

Asn Leu Gln Gln Gln Asn Thr Ala Pro Gln Ile Gly Thr Val Asn Ser
            515                 520                 525

Gln Gly Ala Leu Pro Gly Met Val Trp Gln Asn Arg Asp Val Tyr Leu
        530                 535                 540

Gln Gly Pro Ile Trp Ala Lys Ile Pro His Thr Asp Gly Asn Phe His
545                 550                 555                 560

Pro Ser Pro Leu Met Gly Gly Phe Gly Leu Lys His Pro Pro Pro Gln
                565                 570                 575

Ile Leu Ile Lys Asn Thr Pro Val Pro Ala Asp Pro Pro Thr Thr Phe
            580                 585                 590

Asn Gln Ser Lys Leu Asn Ser Phe Ile Thr Gln Tyr Ser Thr Gly Gln
            595                 600                 605

Val Ser Val Glu Ile Glu Trp Glu Leu Gln Lys Glu Asn Ser Lys Arg
        610                 615                 620

Trp Asn Pro Glu Ile Gln Tyr Thr Ser Asn Tyr Tyr Lys Ser Thr Ser
625                 630                 635                 640

Val Asp Phe Ala Val Asn Thr Glu Gly Val Tyr Ser Glu Pro Arg Pro
                645                 650                 655

Ile Gly Thr Arg Tyr Leu Thr Arg Asn Leu
            660                 665

<210> SEQ ID NO 4
<211> LENGTH: 666
<212> TYPE: PRT
<213> ORGANISM: Adeno-associated virus - 8

<400> SEQUENCE: 4

Met Glu His Asp Lys Ala Tyr Asp Gln Gln Leu Gln Ala Gly Asp Asn
1               5                   10                  15

Pro Tyr Leu Arg Tyr Asn His Ala Asp Ala Glu Phe Gln Glu Arg Leu
                20                  25                  30

Gln Glu Asp Thr Ser Phe Gly Gly Asn Leu Gly Arg Ala Val Phe Gln
            35                  40                  45

Ala Lys Lys Arg Val Leu Glu Pro Leu Gly Leu Val Glu Glu Gly Ala
        50                  55                  60

Lys Thr Ala Pro Gly Lys Lys Arg Pro Val Glu Pro Ser Pro Gln Arg
65                  70                  75                  80

Ser Pro Asp Ser Ser Thr Gly Ile Gly Lys Lys Gly Gln Gln Pro Ala
                85                  90                  95

Arg Lys Arg Leu Asn Phe Gly Gln Thr Gly Asp Ser Glu Ser Val Pro
            100                 105                 110

Asp Pro Gln Pro Leu Gly Glu Pro Pro Ala Ala Pro Ser Gly Val Gly
            115                 120                 125

Pro Asn Thr Met Ala Ala Gly Gly Gly Ala Pro Met Ala Asp Asn Asn
        130                 135                 140

Glu Gly Ala Asp Gly Val Gly Ser Ser Ser Gly Asn Trp His Cys Asp
145                 150                 155                 160

Ser Thr Trp Leu Gly Asp Arg Val Ile Thr Thr Ser Thr Arg Thr Trp
                165                 170                 175

Ala Leu Pro Thr Tyr Asn Asn His Leu Tyr Lys Gln Ile Ser Asn Gly
            180                 185                 190

```
Thr Ser Gly Gly Ala Thr Asn Asp Asn Thr Tyr Phe Gly Tyr Ser Thr
            195                 200                 205

Pro Trp Gly Tyr Phe Asp Phe Asn Arg Phe His Cys His Phe Ser Pro
210                 215                 220

Arg Asp Trp Gln Arg Leu Ile Asn Asn Asn Trp Gly Phe Arg Pro Lys
225                 230                 235                 240

Arg Leu Ser Phe Lys Leu Phe Asn Ile Gln Val Lys Glu Val Thr Gln
                245                 250                 255

Asn Glu Gly Thr Lys Thr Ile Ala Asn Asn Leu Thr Ser Thr Ile Gln
            260                 265                 270

Val Phe Thr Asp Ser Glu Tyr Gln Leu Pro Tyr Val Leu Gly Ser Ala
        275                 280                 285

His Gln Gly Cys Leu Pro Pro Phe Pro Ala Asp Val Phe Met Ile Pro
    290                 295                 300

Gln Tyr Gly Tyr Leu Thr Leu Asn Asn Gly Ser Gln Ala Val Gly Arg
305                 310                 315                 320

Ser Ser Phe Tyr Cys Leu Glu Tyr Phe Pro Ser Gln Met Leu Arg Thr
                325                 330                 335

Gly Asn Asn Phe Gln Phe Thr Tyr Thr Phe Glu Asp Val Pro Phe His
            340                 345                 350

Ser Ser Tyr Ala His Ser Gln Ser Leu Asp Arg Leu Met Asn Pro Leu
        355                 360                 365

Ile Asp Gln Tyr Leu Tyr Tyr Leu Ser Arg Thr Gln Thr Thr Gly Gly
    370                 375                 380

Thr Ala Asn Thr Gln Thr Leu Gly Phe Ser Gln Gly Gly Pro Asn Thr
385                 390                 395                 400

Met Ala Asn Gln Ala Lys Asn Trp Leu Pro Gly Pro Cys Tyr Arg Gln
                405                 410                 415

Gln Arg Val Ser Thr Thr Thr Gly Gln Asn Asn Asn Ser Asn Phe Ala
            420                 425                 430

Trp Thr Ala Gly Thr Lys Tyr His Leu Asn Gly Arg Asn Ser Leu Ala
        435                 440                 445

Asn Pro Gly Ile Ala Met Ala Thr His Lys Asp Asp Glu Glu Arg Phe
    450                 455                 460

Phe Pro Ser Asn Gly Ile Leu Ile Phe Gly Lys Gln Asn Ala Ala Arg
465                 470                 475                 480

Asp Asn Ala Asp Tyr Ser Asp Val Met Leu Thr Ser Glu Glu Glu Ile
                485                 490                 495

Lys Thr Thr Asn Pro Val Ala Thr Glu Glu Tyr Gly Ile Val Ala Asp
            500                 505                 510

Asn Leu Gln Gln Gln Asn Thr Ala Pro Gln Ile Gly Thr Val Asn Ser
        515                 520                 525

Gln Gly Ala Leu Pro Gly Met Val Trp Gln Asn Arg Asp Val Tyr Leu
    530                 535                 540

Gln Gly Pro Ile Trp Ala Lys Ile Pro His Thr Asp Gly Asn Phe His
545                 550                 555                 560

Pro Ser Pro Leu Met Gly Gly Phe Gly Leu Lys His Pro Pro Pro Gln
                565                 570                 575

Ile Leu Ile Lys Asn Thr Pro Val Pro Ala Asp Pro Pro Thr Thr Phe
            580                 585                 590

Asn Gln Ser Lys Leu Asn Ser Phe Ile Thr Gln Tyr Ser Thr Gly Gln
        595                 600                 605
```

Val Ser Val Glu Ile Glu Trp Glu Leu Gln Lys Glu Asn Ser Lys Arg
        610                 615                 620

Trp Asn Pro Glu Ile Gln Tyr Thr Ser Asn Tyr Tyr Lys Ser Thr Ser
625                 630                 635                 640

Val Asp Phe Ala Val Asn Thr Glu Gly Val Tyr Ser Glu Pro Arg Pro
                645                 650                 655

Ile Gly Thr Arg Tyr Leu Thr Arg Asn Leu
                660                 665

<210> SEQ ID NO 5
<211> LENGTH: 69
<212> TYPE: DNA
<213> ORGANISM: Adeno-associated virus - 8

<400> SEQUENCE: 5
gcagcggccc tcgagcacga caaggcctac gaccagcagc tgcaggcggg tgacaatccg    60
tacctgcgg                                                            69

<210> SEQ ID NO 6
<211> LENGTH: 69
<212> TYPE: DNA
<213> ORGANISM: Adeno-associated virus - 1

<400> SEQUENCE: 6
gcagcggccc tcgagcacga caaggcctac gaccagcagc tcaaagcggg tgacaatccg    60
taccttcgg                                                            69

<210> SEQ ID NO 7
<211> LENGTH: 69
<212> TYPE: DNA
<213> ORGANISM: Adeno-associated virus - 6

<400> SEQUENCE: 7
gcagcggccc tcgagcacga caaggcctac gaccagcagc tcaaagcggg tgacaatccg    60
tacctgcgg                                                            69

<210> SEQ ID NO 8
<211> LENGTH: 69
<212> TYPE: DNA
<213> ORGANISM: Adeno-associated virus - 9

<400> SEQUENCE: 8
gcggcggccc tcgagcacga caaggcctac gaccagcagc tcaaggccgg agacaacccg    60
tacctcaag                                                            69

<210> SEQ ID NO 9
<211> LENGTH: 15
<212> TYPE: PRT
<213> ORGANISM: Adeno-associated virus - 8

<400> SEQUENCE: 9

Asn Ala Ala Asp Ala Ala Ala Leu Glu His Asp Lys Ala Tyr Asp
1               5                   10                  15

＃ AAV8 VECTOR WITH ENHANCED FUNCTIONAL ACTIVITY AND METHODS OF USE THEREOF

The present application is § 371 application of PCT/US2012/025088 filed Feb. 14, 2012 which claims priority to U.S. Provisional Application No. 61/442,606 filed Feb. 14, 2011, the entire disclosure of each being incorporated by reference herein.

FIELD OF THE INVENTION

This application relates to the fields of gene therapy and molecular biology. More specifically, this invention provides adeno-associated viral vectors comprising protein capsid variants which accelerate vector breakdown and clearance, thereby reducing undesirable immune responses.

BACKGROUND OF THE INVENTION

Several publications and patent documents are cited throughout the specification in order to describe the state of the art to which this invention pertains. Each of these citations is incorporated herein by reference as though set forth in full.

Gene therapy aims to treat both genetic and infectious diseases via introduction of new genetic material into the appropriate cells in the body. One of the greatest challenges of gene therapy is efficient transfer of genetic material into living cells. Use of recombinant viral vectors for gene delivery significantly improved this process. Two commonly used viral vectors capable of direct in vivo gene transfer are derived from adenovirus (Ad) and adeno-associated virus (AAV). The majority of the 987 worldwide gene therapy trials use viral vectors, 256 use Ad vectors (25.9%) and 25 use AAV vectors (2.5%).

A variety of gene delivery vectors have been developed that can achieve delivery of therapeutic genes to mammalian cells in vitro and in vivo. Some of these are viral vectors which are based on common viruses, for example, adeno-associated virus, Type 2 (AAV2). Structurally, AAV2 is a relatively simple virus, is ubiquitous in the human population and is not known to cause disease. Genetically modified (recombinant) AAV2 has been studied extensively as a gene delivery vector with potential to effectively treat many serious and chronic diseases in humans. More recently additional serotypes of AAV, (e.g., AAV8) have been described that further expand the promise of these vectors for therapeutic gene transfer. Studies performed using a number of different animal models have demonstrated that AAV vectors can mediate transfer and expression of genes encoding therapeutic proteins such as blood coagulation factors VIII (Scallan, et al.) and IX (Herzog et al. 1999; Snyder et al., (1999) and monoclonal antibodies (Lewis et al. 2002) and several other proteins of potential therapeutic clinical benefit. Human clinical trials in which AAV2 vectors expressing human coagulation factor IX were administered confirmed their ability to deliver therapeutic levels of human coagulation factor IX (High et al. 2003; Manno et al. 2006). However, pre-existing immunity to AAV2, and adaptive immune responses to the non-human components (e.g., viral capsid proteins) of AAV-based gene transfer vectors remains a barrier to achieving consistent and efficient gene transfer and long term expression of therapeutic genes in humans. Studies support that rapid degradation and clearance of AAV capsid protein from transduced cells is important to achieve long-term therapeutic transgene expression in humans.

SUMMARY OF THE INVENTION

In accordance with the present invention, an adeno-associated virus (AAV) vector comprising an altered capsid protein is provided, the altered capsid protein reducing the integrity and rigidity of said virus thereby facilitating viral clearance after transduction of a therapeutic transgene. In one embodiment, the vector further comprises a minigene comprising AAV inverted terminal repeats and a heterologous nucleic acid sequence operably linked to regulatory sequences which direct expression of a product from the heterologous nucleic acid sequence in a host cell. In a preferred embodiment, the AAV vector is AAV8, wherein the capsid comprises VP1, VP2, VP3 and VP1.5, the VP1.5 protein having the sequence of amino acids shown in FIG. 5, wherein the amino acid at the amino terminus is either a leucine or a methionine.

In another aspect, the (AAV) vector is selected from the group consisting of AAV1, AAV6 and AAV9, said vector comprising a variant CTG codon in the place of a naturally occurring CTC at position 219 of the nucleotide sequence encoding the cap protein, said vector further comprising a minigene comprising AAV inverted terminal repeats and a heterologous nucleic acid sequence operably linked to regulatory sequences which direct expression of a product from the heterologous nucleic acid sequence in a host cell.

In an alternative approach, the AAV8 vector can comprise a variant CTG start codon or an ATG start codon at position 177 of the nucleotide sequence encoding the cap protein. In this variant, the natural (wild type) start codon at position 1 of the nucleotide sequence encoding the cap protein is optionally altered such that it can no longer function as a start codon. In a preferred embodiment, the start codon is eliminated completely. In yet another approach, the nucleic acid encoding amino acids 1-177 can be eliminated and the novel start codon described herein employed to encode VP1.5. The resulting vector further comprises a minigene comprising AAV inverted terminal repeats and a heterologous nucleic acid sequence operably linked to regulatory sequences which direct expression of a product from the heterologous nucleic acid sequence in a host cell.

In an alternative approach, a modified AAV of any of the serotypes AAV1, AAV2, AAV3, AAV4, AAV5, AAV6, AAV7, AAV8, AAV9, or any other known AAV serotypes, that comprises a CTG start codon or an ATG start codon at position 177, or a position within 100 nucleotides of position 177 of the nucleotide sequence encoding the cap protein, wherein the natural (wild type) start codon at position 1 of the corresponding nucleotide sequence encoding the cap protein is obliterated is disclosed. The resulting AAV particles will be composed of three types of capsid proteins, namely VP1.5, VP2 and VP3, lacking capsid protein VP1 altogether. Said vectors further comprising a minigene comprising AAV inverted terminal repeats and a heterologous nucleic acid sequence operably linked to regulatory sequences which direct expression of a product from the heterologous nucleic acid sequence in a host cell.

In an alternative approach, a modified AAV of any serotype, including without limitation, AAV1, AAV2, AAV3, AAV4, AAV5, AAV6, AAV7, AAV8, AAV9, that comprises a CTG start at position 177, and a chimeric, spacer sequence between positions 1 and position 177 is provided. Said vectors further comprise a minigene comprising AAV inverted terminal repeats and a heterologous nucleic acid sequence operably linked to regulatory sequences which direct expression of a product from the heterologous nucleic acid sequence in a host cell.

In a preferred embodiment, the AAV vectors of the invention comprising the variant capsid proteins are useful for expression of therapeutic peptides. Such peptides include, without limitation, an anti-viral RNAi molecule, Factor VIII, Factor IX or a functional fragment thereof. Additional expression products include for example, IgG, IgM, IgA, IgD, IgE, chimeric immunoglobulins, humanized antibodies, or single chain antibodies. In one aspect the expression product is an RNAI that is useful for inhibiting HCV infection and replication.

In another embodiment of the invention, a pharmaceutical composition comprising the AAV vector of the invention in a biologically compatible carrier is provided. Also encompassed by the present invention are cell cultures comprising the vectors disclosed herein.

The invention also encompasses a method of delivering a transgene to a cell in a subject, said method comprising the step of contacting the cell with an AAV vector as disclosed herein, wherein said AAV vector comprises the transgene, wherein the presence of vp1.5 in said vector is associated with a reduced anti-capsid IgG response.

BRIEF DESCRIPTION OF THE DRAWINGS

FIG. 2. Sequence alignment showing canonical nucleotide sequence for AAV8 (AAV8-cap) (SEQ ID NO:1), compared with the sequence found for pAAV8PK (SEQ ID NO:2), SeqWright Jul08 (AAV8.1). In this alignment, the base C at position 219 of the reported AA V8 Cap nucleotide sequence (corresponding to position 2339 in the AA VS genome sequence reported in FIG. 1B in U.S. Pat. No. 7,790,449 (Gao et al) and in GeneBank AF513852.1), of the codon CTC, has changed to the base G, resulting in an in-frame codon 'CTG' known to act as an alternative start codon (Claus et 25 al, 2003). Both these codons encode the amino acid leucine (L), located in the sequence NAADAAALEHDKAYD (SEQ ID NO:9), corresponding to amino acid position 73 of AAV8 VP1 as reported in FIG. 2A in U.S. Pat. No. 7,790,449 (Gao et al). The codon CTG appears to act as an unexpected start codon in mammalian cells used to generate AA V vectors.

FIG. 4. Assessment of ability of AA V8 vectors encoding human coagulation factor IX (hF.IX) to transduce and express circulating hF.IX following administration to mice. (A) shows level of circulating hF.IX as determined by ELISA at 2, 4 and 6 weeks post vector administration for AA V8-hFIX vector Lot KA434 (control) and AA V-hFIX vector Lot KA535 (AAV8.1-novel vector containing the VP1.5 capsid proteins).

FIG. 5 shows the amino acid sequence of VP 1.5. Panel A (SEQ ID NO:3), shows the predicted sequence assuming that variant codon CTG encodes the amino acid Leucine. Panel B (SEQ ID NO:4), shows the predicted amino sequence assuming that variant codon CTG encodes amino acid Methionine, predicted because it is the first amino acid in the variant polypeptide.

FIG. 6 shows the sequence alignment of AAVI (SEQ ID NO:6), AAV6 (SEQ ID NO:7), AAV8 (SEQ ID NO:5) and AAV9 (SEQ ID NO:8). As shown by the boxed regions, the CTC codon described in FIG. 2 is conserved in each of these AAV serotypes. It is predicted that these other serotypes can be altered by substitution of C at position 219 with G, by site directed mutagenesis of the nucleotide sequence. This change is predicted to generate capsids containing an additional VP band in these other serotypes corresponding to VPI 0.5 described for AAV8. 1, resulting in novel altered structure and reduced rigidity, and predicted to facilitate transduction and long-term expression of trans genes in these other serotypes.

FIG. 7 shows the location of another CTC codon in the AAV8 Cap (SEQ ID NO:1) nucleotide sequence (boxed). Changing nucleotide C at position 177 to a G in AAV8 is predicted to introduce a start codon, resulting in a novel modified capsid composition comprising four capsid polypeptides that is advantageous. Changing nucleotide C at position 177 to a G in AAV8.1 (SEQ ID NO:2) is predicted to 30 introduce another start codon, resulting in another novel modified capsid composition comprising five capsid polypeptides that is advantageous in gene therapy applications.

DETAILED DESCRIPTION OF THE INVENTION

Figure 1:
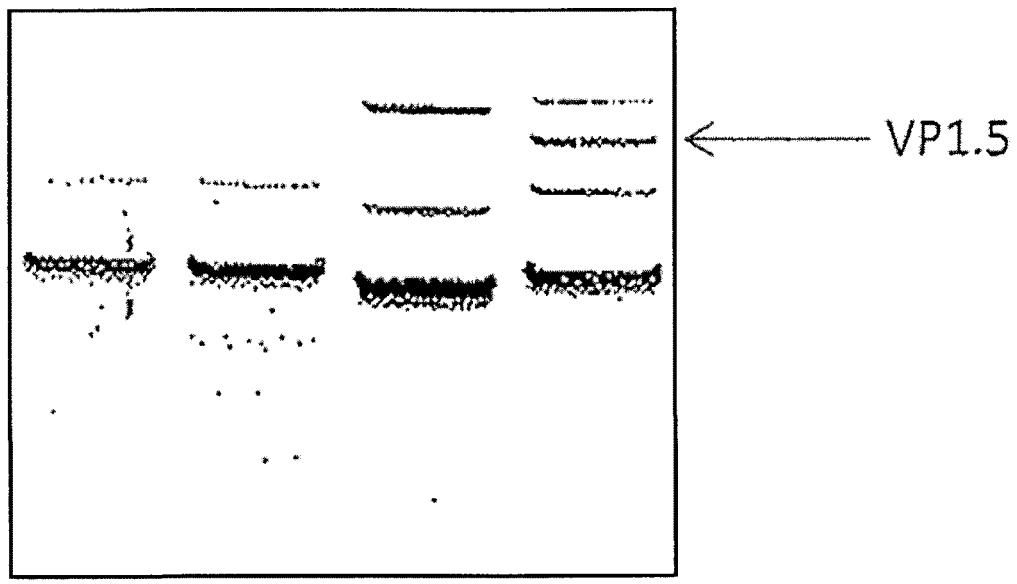
FIG. 1. Representative SDS PAGE silver stained gel showing VP1.5, an AAV VP band intermediate in position between canonical bands VP1 and VP2.
Figure 3:
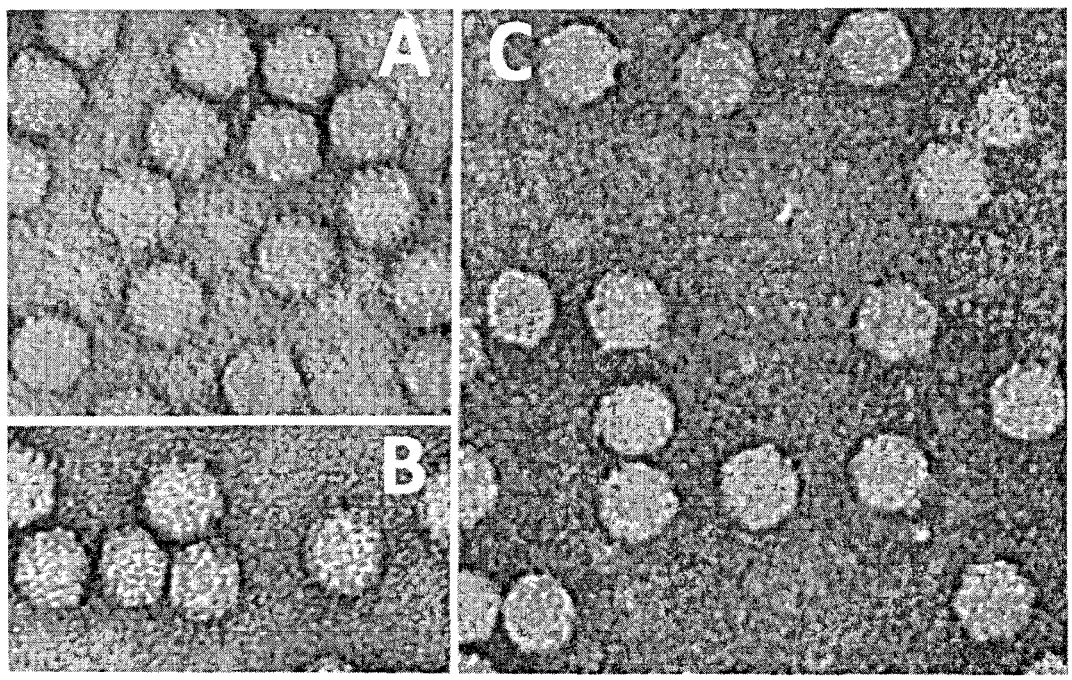
FIG. 3. Electron micrographs of negatively stained purified AA V particles. (A) shows normal AAV8 vectors (AAV8 control); (B) shows normal AAV2 vectors (AA V2 control); and (C) shows variant AA V8 vectors (AAV8.1) containing the VP1.5 capsid protein. The AAV8.1 vectors containing the VP1.5 capsid are less symmetrical than control AAV vectors lacking this mutation, and demonstrate evidence of vector particle fragmentation, supporting less stable capsid architecture.

The present invention provides a novel and improved AAV vector composition for use in gene therapy protocols. Human clinical trials in which AAV8 vectors expressing human coagulation factor IX were administered have been initiated, with promising preliminary results reported (Nathwani et al. 2010). Based on previous clinical studies with AAV2 (Manno et al, 2006), degradation of the AAV capsid proteins that was not sufficiently rapid to clear the capsid proteins before cellular immune effectors recognized and eliminated the transduced cells may have contributed to the failure to achieve long-term transgene expression in humans. In the present invention, a single nucleotide exchange in the gene encoding for AAV8 cap was found to result in an additional start codon (CTG). We refer to this variant AAV8 vector as AAV8.1. The canonical VP distribution in AAV vectors is VP1, VP2, and VP3, three N-terminal variants resulting from differential start sites during AAV cap transcription. Each AAV particle is made up of approximately 60 total VP proteins comprising VP1, VP2, and VP3 (three polypeptide species) at the following approximate protein ratios: 5 VP1+5 VP2+50 VP3. In the case of AAV8.1, the single nucleotide change appears to give one additional VP protein, intermediate in length between VP1 and VP2. Herein, the variant VP protein apparently unique to AAV8.1 will be referred to as VP 1.5. The novel VP1.5 polypeptide is present in AAV8.1 at comparable amounts to VP1 and VP2. It appears that the inclusion of this variant VP protein in the capsid structure does not alter the functional activity as measured by transduction in vivo in mice, but appears to slightly alter the integrity and/or reduce the rigidity of the capsid, which should result in accelerated disassembly and clearance of the virus after transduction of the transgene. Accelerated clearance should in turn reduce or eliminate deleterious immune effector functions following clinical vector administration. The altered integrity/reduced rigidity of AAV8.1 should also facilitate improved packaging of therapeutic DNA that exceeds the normal packaging limit (approximately 4.7 kb) of AAV8 vectors.

I. Definitions

"Gene therapy" is the insertion of genes into an individual's cells and/or tissues to treat a disease, commonly hereditary diseases wherein a defective mutant allele is replaced or supplemented with a functional one.

"Adeno-associated viruses", from the parvovirus family, are small viruses with a genome of single stranded DNA. These viruses can insert genetic material at a specific site on chromosome 19 and are preferred because they are not associated with pathogenic disease in humans.

A "human protein" for use in the vectors of the invention is preferably a highly conserved protein which would not be recognized as a foreign or non-self antigen by the human immune system. While human serum albumin is exemplified herein, other proteins which would be useful for this purpose include, without limitation, include fibrinogen A, fibrinogen B, beta-2-microglobulin, zinc-alpha-2-glycoprotein, alpha-2-HS-glycoprotein (fetuin), serum amyloid protein A, haptoglobin, profilin, desmocollin, thymosin beta-4 and -beta-10, apolipoprotein C-III, uteroglobin, ubiquitin, gelsolin, collagen, fibrin, as well as fragments of these and other human proteins.

A "therapeutic" peptide or protein is a peptide or protein that may alleviate or reduce symptoms that result from an absence or defect in a protein in a cell or subject. Alternatively, a "therapeutic" peptide or protein is one that otherwise confers a benefit to a subject, e.g., anti-cancer effects. Therapeutic peptides and proteins include, but are not limited to, CFTR (cystic fibrosis transmembrane regulator protein), dystrophin (including the protein product of dystrophin mini-genes, see, e.g, Vincent et al., (1993) Nature Genetics 5:130), utrophin (Tinsley et al., (1996) Nature 384:349), clotting factors (Factor XIII, Factor IX, Factor X, etc.), monoclonal antibodies (Lewis et al., 2002), erythropoietin, the LDL receptor, lipoprotein lipase, ornithine transcarbamylase, β-globin, α-globin, spectrin, α-antitrypsin, adenosine deaminase, hypoxanthine guanine phosphoribosyl transferase, β-glucocerebrosidase, sphingomyelinase, lysosomal hexosaminidase, branched-chain keto acid dehydrogenase, hormones, growth factors (e.g., insulin-like growth factors 1 and 2, platelet derived growth factor, epidermal growth factor, nerve growth factor, neurotrophic factor −3 and −4, brain-derived neurotrophic factor, glial derived growth factor, transforming growth factor α and β, and the like), cytokines (e.g., α-interferon, β-interferon, interferon-γ, interleukin-2, interleukin-4, interleukin 12, granulocyte-macrophage colony stimulating factor, lymphotoxin), suicide gene products (e.g., herpes simplex virus thymidine kinase, cytosine deaminase, diphtheria toxin, cytochrome P450, deoxycytidine kinase, and tumor necrosis factor), proteins conferring resistance to a drug used in cancer therapy, tumor suppressor gene products (e.g., p53, Rb, Wt-1, NF1, VHL, APC, and the like), and any other peptide or protein that has a therapeutic effect in a subject in need thereof.

Further exemplary therapeutic peptides or proteins include those that may used in the treatment of a disease condition including, but not limited to, cystic fibrosis (and other diseases of the lung), hemophilia A, hemophilia B, thalassemia, anemia and other blood disorders, AIDS, Alzheimer's disease, Parkinson's disease, Huntington's disease, amyotrophic lateral sclerosis, epilepsy, and other neurological disorders, cancer, diabetes mellitus, muscular dystrophies (e.g., Duchenne, Becker), Gaucher's disease, Hurler's disease, adenosine deaminase deficiency, glycogen storage diseases and other metabolic defects, retinal degenerative diseases (and other diseases of the eye), and diseases of solid organs (e.g., brain, liver, kidney, heart).

The term "promoters" or "promoter" as used herein can refer to a DNA sequence that is located adjacent to a DNA sequence that encodes a recombinant product. A promoter is preferably linked operatively to an adjacent DNA sequence. A promoter typically increases an amount of recombinant product expressed from a DNA sequence as compared to an amount of the expressed recombinant product when no promoter exists. A promoter from one organism can be utilized to enhance recombinant product expression from a DNA sequence that originates from another organism. For example, a vertebrate promoter may be used for the expression of jellyfish GFP in vertebrates. In addition, one promoter element can increase an amount of recombinant products expressed for multiple DNA sequences attached in tandem. Hence, one promoter element can enhance the expression of one or more recombinant products. Multiple promoter elements are well-known to persons of ordinary skill in the art.

In one embodiment, high-level constitutive expression will be desired. Examples of such promoters include, without limitation, the retroviral Rous sarcoma virus (RSV) LTR promoter/enhancer, the cytomegalovirus (CMV) immediate early promoter/enhancer (see, e.g., Boshart et al, Cell, 41:521-530 (1985)), the SV40 promoter, the dihydrofolate reductase promoter, the cytoplasmic β-actin promoter and the phosphoglycerol kinase (PGK) promoter.

In another embodiment, inducible promoters may be desired. Inducible promoters are those which are regulated by exogenously supplied compounds, either in cis or in trans, including without limitation, the zinc-inducible sheep metallothionine (MT) promoter; the dexamethasone (Dex)-inducible mouse mammary tumor virus (MMTV) promoter; the T7 polymerase promoter system (WO 98/10088); the tetracycline-repressible system (Gossen et al, Proc. Natl. Acad. Sci. USA, 89:5547-5551 (1992)); the tetracycline-inducible system (Gossen et al., Science, 268:1766-1769 (1995); see also Harvey et al., Curr. Opin. Chem. Biol., 2:512-518 (1998)); the RU486-inducible system (Wang et al., Nat. Biotech., 15:239-243 (1997) and Wang et al., Gene Ther., 4:432-441 (1997)]; and the rapamycin-inducible system (Magari et al., J. Clin. Invest., 100:2865-2872 (1997); Rivera et al., Nat. Medicine. 2:1028-1032 (1996)). Other types of inducible promoters which may be useful in this context are those which are regulated by a specific physiological state, e.g., temperature, acute phase, or in replicating cells only.

In another embodiment, the native promoter for the transgene or nucleic acid sequence of interest will be used. The native promoter may be preferred when it is desired that expression of the transgene or the nucleic acid sequence should mimic the native expression. The native promoter may be used when expression of the transgene or other nucleic acid sequence must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

In one embodiment, the recombinant viral genome comprises a transgene operably linked to a tissue-specific promoter. For instance, if expression in skeletal muscle is desired, a promoter active in muscle may be used. These include the promoters from genes encoding skeletal α-actin, myosin light chain 2A, dystrophin, muscle creatine kinase, as well as synthetic muscle promoters with activities higher than naturally-occurring promoters. See Li et al., Nat. Biotech., 17:241-245 (1999). Examples of promoters that are tissue-specific are known for liver albumin, Miyatake et al. J. Virol., 71:5124-32 (1997); hepatitis B virus core promoter, Sandig et al., Gene Ther. 3:1002-9 (1996); alpha-fetoprotein (AFP), Arbuthnot et al., Hum. Gene Ther., 7:1503-14 (1996)], bone (osteocalcin, Stein et al., Mol. Biol. Rep., 24:185-96 (1997); bone sialoprotein, Chen et al., J. Bone Miner. Res. 11:654-64 (1996)), lymphocytes (CD2, Hansal et al., J. Immunol., 161:1063-8 (1998); immunoglobulin heavy chain; T cell receptor a chain), neuronal (neuron-specific enolase (NSE) promoter, Andersen et al. Cell. Mol. Neurobiol., 13:503-15 (1993); neurofilament light-chain gene, Piccioli et al., Proc. Natl. Acad. Sci. USA, 88:5611-5 (1991); the neuron-specific vgf gene, Piccioli et al., Neuron, 15:373-84 (1995)]; among others.

The term "enhancers" or "enhancer" as used herein can refer to a DNA sequence that is located adjacent to the DNA sequence that encodes a recombinant product. Enhancer elements are typically located upstream of a promoter element or can be located downstream of or within a coding DNA sequence (e.g., a DNA sequence transcribed or translated into a recombinant product or products). Hence, an enhancer element can be located 100 base pairs, 200 base pairs, or 300 or more base pairs upstream or downstream of a DNA sequence that encodes recombinant product. Enhancer elements can increase an amount of recombinant product expressed from a DNA sequence above increased expression afforded by a promoter element. Multiple enhancer elements are readily available to persons of ordinary skill in the art.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism.

A "vector" is a replicon, such as a plasmid, cosmid, bacmid, phage or virus, to which another genetic sequence or element (either DNA or RNA) may be attached so as to bring about the replication of the attached sequence or element.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

The terms "transform", "transfect", "transduce", shall refer to any method or means by which a nucleic acid is introduced into a cell or host organism and may be used interchangeably to convey the same meaning. Such methods include, but are not limited to, transfection, electroporation, microinjection, infection, PEG-fusion and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. Finally, the introduced nucleic acid may exist in the recipient cell or host organism only transiently.

The term "selectable marker gene" refers to a gene that when expressed confers a selectable phenotype, such as antibiotic resistance, on a transformed cell or plant.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g. enhancers) in an expression vector.

The term "oligonucleotide" as used herein refers to sequences, primers and probes of the present invention, and is defined as a nucleic acid molecule comprised of two or more ribo- or deoxyribonucleotides, preferably more than three. The exact size of the oligonucleotide will depend on various factors and on the particular application and use of the oligonucleotide.

The phrase "specifically hybridize" refers to the association between two single-stranded nucleic acid molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence.

The term "primer" as used herein refers to a DNA oligonucleotide, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3' terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able to anneal with the desired template strand in a manner sufficient to provide the 3' hydroxyl moiety of the primer in appropriate juxtaposition for use in the initiation of synthesis by a polymerase or similar enzyme. It is not required that the primer sequence represent an exact complement of the desired template. For example, a non-complementary nucleotide sequence may be attached to the 5' end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product.

Polymerase chain reaction (PCR) has been described in U.S. Pat. Nos. 4,683,195, 4,800,195, and 4,965,188, the entire disclosures of which are incorporated by reference herein.

The term "isolated" may refer to a compound or complex that has been sufficiently separated from other compounds with which it would naturally be associated. "Isolated" is not meant to exclude artificial or synthetic mixtures with other compounds or materials, or the presence of impurities that do not interfere with fundamental activity or ensuing assays, and that may be present, for example, due to incomplete purification, or the addition of stabilizers. The term "immune response" is meant to refer to any response to an antigen or antigenic determinant by the immune system of a vertebrate subject. Exemplary immune responses include humoral immune responses (e.g. production of antigen-specific antibodies) and cell-mediated immune responses (e.g. lymphocyte proliferation), as defined herein below.

II. Methods of Using and Methods of Administration of the Variant Adenoassociated Viral Vectors of the Invention The methods of the present invention provide a means for delivering heterologous nucleic acid sequences into a broad range of host cells, including both dividing and non-dividing cells. The vectors and other reagents, methods and pharmaceutical formulations of the present invention are additionally useful in a method of administering a protein or peptide to a subject in need thereof, as a method of treatment or otherwise. In this manner, the protein or peptide may thus be produced in vivo in the subject. The subject may be in need of the protein or peptide because the subject has a deficiency of the protein or peptide, or because the production of the protein or peptide in the subject may impart some therapeutic effect, as a method of treatment or otherwise, and as explained further below.

In general, the present invention may be employed to deliver any foreign nucleic acid with a biological effect to treat or ameliorate the symptoms associated with any disorder related to gene expression. Illustrative disease states include, but are not limited to: cystic fibrosis (and other diseases of the lung), hemophilia A, hemophilia B, thalassemia, anemia and other blood coagulation disorders, AIDs, Alzheimer's disease, Parkinson's disease, Huntington's disease, amyotrophic lateral sclerosis, epilepsy, and other neurological disorders, cancer, diabetes mellitus, muscular dystrophies (e.g., Duchenne, Becker), Gaucher's disease, Hurler's disease, adenosine deaminase deficiency, glycogen storage diseases and other metabolic defects, retinal degenerative diseases (and other diseases of the eye), diseases of solid organs (e.g., brain, liver, kidney, heart), and the like.

In addition, the present invention may be employed to deliver nucleic acids encoding monoclonal antibodies or fragments thereof that are known to provide beneficial biological effects to treat or ameliorate the symptoms associated with cancers, infectious diseases, and autoimmune diseases such as rheumatoid arthritis.

Gene transfer has substantial potential use in understanding and providing therapy for disease states. There are a number of inherited diseases in which defective genes are known and have been cloned. In some cases, the function of these cloned genes is known. In general, the above disease states fall into two classes: deficiency states, usually of enzymes, which are generally inherited in a recessive manner, and unbalanced states, at least sometimes involving regulatory or structural proteins, which are inherited in a dominant manner. For deficiency state diseases, gene transfer could be used to bring a normal gene into affected tissues for replacement therapy, as well as to create animal models for the disease using antisense mutations. For unbalanced disease states, gene transfer could be used to create a disease state in a model system, which could then be used in efforts to counteract the disease state. Thus the methods of the present invention permit the treatment of genetic diseases. As used herein, a disease state is treated by partially or wholly remedying the deficiency or imbalance that causes the disease or makes it more severe. The use of site-specific integration of nucleic sequences to cause mutations or to correct defects is also possible.

Finally, the instant invention finds further use in diagnostic and screening methods, whereby a gene of interest is transiently or stably expressed in a cell culture system, or alternatively, a transgenic animal model.

III. Subjects, Pharmaceutical Formulations, Vaccines, and Modes of Administration The present invention finds use in both veterinary and medical applications. Suitable subjects include both avians and mammals, with mammals being preferred. The term "avian" as used herein includes, but is not limited to, chickens, ducks, geese, quail, turkeys and pheasants. The term "mammal" as used herein includes, but is not limited to, humans, bovines, ovines, caprines, equines, felines, canines, lagomorphs, etc. Human subjects are the most preferred. Human subjects include fetal, neonatal, infant, juvenile and adult subjects.

In particular embodiments, the present invention provides a pharmaceutical composition comprising a virus particle of the invention in a pharmaceutically-acceptable carrier or other medicinal agents, pharmaceutical agents, carriers, adjuvants, diluents, etc. For injection, the carrier will typically be a liquid. For other methods of administration, the carrier may be either solid or liquid, such as sterile, pyrogen-free water or sterile pyrogen-free phosphate-buffered saline solution. For inhalation administration, the carrier will be respirable, and will preferably be in solid or liquid particulate form. As an injection medium, it is preferred to use water that contains the additives usual for injection solutions, such as stabilizing agents, salts or saline, and/or buffers.

In other embodiments, the present invention provides a pharmaceutical composition comprising a cell in which an AAV provirus is integrated into the genome in a pharmaceutically-acceptable carrier or other medicinal agents, pharmaceutical agents, carriers, adjuvants, diluents, etc.

By "pharmaceutically acceptable" it is meant a material that is not biologically or otherwise undesirable, e.g., the material may be administered to a subject without causing any undesirable biological effects. Thus, such a pharmaceutical composition may be used, for example, in transfection of a cell ex vivo or in administering a viral particle or cell directly to a subject.

The present invention further provides a method of delivering a nucleic acid to a cell. For in vitro methods, the virus—may be administered to the cell by standard viral transduction methods, as are known in the art. Preferably, the virus particles are added to the cells at the appropriate multiplicity of infection according to standard transduction methods appropriate for the particular target cells. Titers of virus to administer can vary, depending upon the target cell type and the particular virus vector, and may be determined by those of skill in the art without undue experimentation. Alternatively, administration of a parvovirus vector of the present invention can be accomplished by any other means known in the art.

Recombinant virus vectors are preferably administered to the cell in a biologically-effective amount. A "biologically-effective" amount of the virus vector is an amount that is sufficient to result in infection (or transduction) and expression of the heterologous nucleic acid sequence in the cell. If the virus is administered to a cell in vivo (e.g., the virus is administered to a subject as described below), a "biologically-effective" amount of the virus vector is an amount that is sufficient to result in transduction and expression of the heterologous nucleic acid sequence in a target cell.

The cell to be administered the inventive virus vector may be of any type, including but not limited to neural cells (including cells of the peripheral and central nervous systems, in particular, brain cells), lung cells, retinal cells, epithelial cells (e.g., gut and respiratory epithelial cells), muscle cells, pancreatic cells (including islet cells), hepatic cells, myocardial cells, bone cells (e.g., bone marrow stem cells), hematopoietic stem cells, spleen cells, keratinocytes, fibroblasts, endothelial cells, prostate cells, germ cells, and the like. Alternatively, the cell may be any progenitor cell. As a further alternative, the cell can be a stem cell (e.g., neural stem cell, liver stem cell). Moreover, the cells can be from any species of origin, as indicated above.

In particular embodiments of the invention, cells are removed from a subject, the parvovirus vector is introduced therein, and the cells are then replaced back into the subject. Methods of removing cells from subject for treatment ex vivo, followed by introduction back into the subject are known in the art. Alternatively, the rAAV vector is introduced into cells from another subject, into cultured cells, or into cells from any other suitable source, and the cells are administered to a subject in need thereof.

Suitable cells for ex vivo gene therapy include, but are not limited to, liver cells, neural cells (including cells of the central and peripheral nervous systems, in particular, brain cells), pancreas cells, spleen cells, fibroblasts (e.g., skin fibroblasts), keratinocytes, endothelial cells, epithelial cells, myoblasts, hematopoietic cells, bone marrow stromal cells, progenitor cells, and stem cells.

Dosages of the cells to administer to a subject will vary upon the age, condition and species of the subject, the type of cell, the nucleic acid being expressed by the cell, the mode of administration, and the like. Typically, at least about $10^2$ to about $10^8$, preferably about $10^3$ to about $10^6$ cells, will be administered per dose. Preferably, the cells will be administered in a "therapeutically-effective amount".

A "therapeutically-effective" amount as used herein is an amount of that is sufficient to alleviate (e.g., mitigate, decrease, reduce) at least one of the symptoms associated with a disease state. Alternatively stated, a "therapeutically-effective" amount is an amount that is sufficient to provide some improvement in the condition of the subject.

A further aspect of the invention is a method of treating subjects in vivo with the inventive virus particles. Administration of the parvovirus particles of the present invention to a human subject or an animal in need thereof can be by any means known in the art for administering virus vectors.

Exemplary modes of administration include oral, rectal, transmucosal, topical, transdermal, inhalation, parenteral (e.g., intravenous, subcutaneous, intradermal, intramuscular, and intraarticular) administration, and the like, as well as direct tissue or organ injection, alternatively, intrathecal, direct intramuscular, intraventricular, intravenous, intraperitoneal, intranasal, or intraocular injections. Injectables can be prepared in conventional forms, either as liquid solutions or suspensions, solid forms suitable for solution or suspenions in liquid prior to injection, or as emulsions. Alternatively, one may administer the virus in a local rather than systemic manner, for example in a depot or sustained-release formation.

In particularly preformed embodiments of the invention, the nucleotide sequence of interest is delivered to the liver of the subject. Administration to the liver may be achieved by any method known in art, including, but not limited to intravenous administration, intraportal administration, intrabilary administration, intra-arterial administration, and direct injection into the liver paraenchyma.

Preferably, the cells (e.g., liver cells) are infected by a recombinant parvovirus vector encoding a peptide or protein, the cells express the encoded peptide or protein and secrete it into the circulatory system in a therapeutically-effective amount (as defined above). Alternatively, the vector is delivered to and expressed by another cell or tissue, including but not limited to, brain, pancreas, spleen or muscle.

In other preferred embodiments, the inventive parovirus particles are administered intramuscularly, more preferably by intramuscular injection or by local administration (as defined above). In other preferred embodiments, the parovirus particles of the present invention are administered to the lungs.

The parovirus vector disclosed herein may be administered to the lungs of a subject by any suitable means, but are preferably administered by adminsitering an aerosol suspension of respirable particles comprised of the inventive parovirus vectors, which the subject inhales. The respirable particles may be liquid or solid. Aerosols of liquid particles comprising the inventive parovirus vectors may be produced by any suitable means, such as with a pressure-driven aerosol nebulizer or an ultrasonic nebulizer, as is known to those of skill in art. See, e.g. U.S. Pat. No. 4,501,729. Aerosols of solid particles comprising the inventive virus vectors may likewise be produced with any solid particulate medicament aerosol generator, by techniques known in the pharmaceutical art.

Dosages of the inventive parvovirus particles will depend upon the mode of administration, the disease or condition to be treated, the individual subject's condition, the particular virus vector, and the gene to be delivered and can be determined in a routine manner. Exemplary doses for achieving therapeutic effects are virus titers of at least about $10^5$, $10^6$, $10^7$, $10^8$, $10^9$, $10^{10}$, $10^{11}$, $10^{12}$, $10^{13}$, $10^{14}$, $10^{15}$, $10^{16}$ transducting units or more, preferably about $10^8$ to $10^{13}$ transducting units, yet more preferably $10^{12}$ transducing units.

In particular embodiments of the invention, more than one administration (e.g., two, three, four, or more administrations) may be employed to achieve therapeutic levels of gene expression. According to this embodiment and as described above the VP 1.5 containing parvoviruses of the present invention are administered to reduce the occurrence of neutralizing antibodies in the subject to be treated or to prevent the development of an immune response in the subject. The subject may be presented with seemingly new virus vectors by packaging the rAAV genome within an array of hybrid or chimeric parvovirus capsids.

In summary, the parvovirus vectors, reagents, and methods of the present invention can be used to direct a nucleic acid to either dividing or non-dividing cells, and to stably express the heterologous nucleic acid therein. Using this vector system, it is now possible to introduce into cells, in vitro or in vivo, genes that encode proteins that affect cell physiology. The vectors of the present invention can thus be useful in gene therapy for disease states or for experimental modification of cell physiology.

The following example is provided to illustrate certain embodiments of the invention. It is not intended to limit the invention in anyway.

EXAMPLE

A Capsid Composition Variant Containing Four VP Proteins Caused by a Novel Start Codon at Position 219 of the Nucleotide Sequence of AAV8 Cap Recombinant adeno-associated virus serotype 8 vectors generated by transient transfection of HEK293 cells and purified extensively by combined column chromatography and gradient ultracentrifugation steps were observed to contain a VP band in addition to the canonical VP1, 2 and 3, when assessed by SDS-PAGE/silver staining. The additional band migrated at a position intermediate between the VP1 and VP2, was determined to be a VP protein by Western blotting using monoclonal antibody B1, and was designated "VP1.5". See FIG. 1 and FIG. 5. Sequencing of the packaging plasmid used to generate this vector indicated a single nucleotide difference from the expected AAV8 Cap sequence, with G replacing C at position 219. This nucleotide exchange is not predicted to change the amino acid sequence of the encoded proteins, except for the possibility that, if creating a start codon, the amino acid methionine is likely to occur in the amino terminal position of a new polypeptide. This nucleotide change does result in a CTG codon that has been described as an alternative start codon (Clause et al, 2003), and appears to act as a start codon at a position intermediate between the VP1 and VP2 start codons in the mammalian cells used to produce vector. Estimated by band intensity using silver staining, or Coomassie blue staining (with higher loading) of SDS-PAGE gels, the anomalous VP1.5 band was present at a comparable quantity to VP1 and VP2. Dynamic light scattering analysis to assess particle size indicated that highly purified AAV8 particles containing VP1.5 were comparable to normal recombinant AAV8, both demonstrating an approximate radius of 13 nm. Examination of normal and VP1.5-containing AAV8 particles by negative staining electron microscopy indicated similar size and morphology; however, some loss of homogeneous structure and symmetry, and increased evidence of fragmentation in the variant (AAV8.1) particles was noted, observations consistent with lower capsid stability.

In a side by side experiment to characterize the functional activity of the VP1.5 variant (see FIG. 4), a human coagulation FIX expression cassette driven by the liver-specific human Alpha 1 Anti-Trypsin (hAAT) promoter was packaged using normal or VP1.5 variant capsids and the vectors were purified using an optimized double cesium gradient ultracentrifugation purification method (Grimm et al, 2005; Ayuso et al, 2010). Based on titering by two methods (protein based and qPCR) to ensure comparability, the respective vectors were injected via tail vein in B57/B16 mice at a dose of $2.5 \times 10^{10}$ vg/mouse (five mice per dose). Both vectors resulted in indistinguishable, high level expression of hFIX at all time points tested (2, 4 and 6 weeks), with >75 ug/mL of circulating hFIX measured at week 6. Animals receiving the variant capsid showed a lower anti-capsid IgG response than AAV8-injected mice. These data characterize a novel capsid composition observed in recombinant AAV8, caused by a novel translational start codon in Cap, that retains normal structure and functional activity.

Site directed mutagenesis was performed on a vector packaging plasmid containing the sequences for AAV rep and AAV8 cap, and appropriate promoters, to change the ATG sequence at position 1 of AAV8 cap to GGG, or any other codon that is not a start codon, and to change the natural (wild type) codon at position 177 of AAV8 cap from 'CTC' to 'CTG' or 'ATG', thus introducing a start codon at this position. This modified vector packaging plasmid is used for generation along with a helper plasmid encoding required helper virus functions, and a vector plasmid encoding a vector genome comprising a human coagulation factor IX expression cassette, by helper virus free transient transfection of HEK293 cells, and the resulting vector purified, as has been described previously (reviewed in Wright J F (2009) Transient transfection methods for clinical AAV vector production. Human Gene Therapy 20:698-706). The resulting purified vectors, composed of VP1.5, VP2 and VP3, are manufactured and subjected to appropriate characterization and Quality Control testing, as has been described previously (reviewed in Wright J F (2008) Manufacturing and characterizing AAV-based vector for use in clinical studies. Gene Therapy 15:840-848.) The vector is administered to persons with hemophilia B to effect therapeutic gene transfer, resulting in amelioration of symptoms of their hemophilia B disease.

These data indicate that capsid protein VP length and composition may be exploited to further optimize recombinant vectors, thereby providing improved delivery of therapeutic transgenes to patients in need of such treatment.

REFERENCES

Nathwani, A., Tuddenham, E., Rosales, C., McIntosh, J., Riddell, A., Rustgi, P., Glader, B., Kay, M., Allay, J., Coleman, J., Sleep, S., High, K. A., Mingozzi, F., Gray, J. T., Reiss, U. M., Nienhuis, A. W., Davidoff, A., 2010. Early clinical trial results following administration of a low dose of a novel self complementary adeno-associated viral vector encoding human Factor IX in two subjects with severe hemophilia B. Blood 116, 114.

Manno, C. S., Arruda, V. R., Pierce, G. F, Glader, B., Ragni, M., Rasko, J., Ozelo, M. C., Hoots, K., Blatt, P. Konkle, B., Dake, M., Kaye, R., Razavi, M., Zajko, A., Zehnder, J. Nakai, H., Chew, A., Leonard, D., Wright, J. F., Lessard, R. R, Sommer J. M., Tigges, M., Sabatino, D., Luk, A., Jiang, H., Mingozzi, F., Couto, L, Ertl, H. C., High, K. A., Kay, M. A., 2006. Successful transduction of liver in hemophilia by AAV-factor IX and limitations imposed by the host immune response. Nature Medicine 12: 342-347.

Claus, P, Doring F, Gringel S, Muller-Ostermeyer F, Fuhlrott J, Kraft T, Grothe C., 2003. Differential intranuclear localization of fibroblast growth factor-2 isoforms and specific interactions with the survival of motoneuron protein. Journal of Biological Chemistry 278:479-485.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A recombinant adeno-associated virus (rAAV) vector comprising,
   a) capsid proteins VP1, VP2, VP3 and VP1.5
      (i) of a serotype selected from the group consisting of AAV8, AAV1, AAV6 and AAV9, said VP1.5 protein translated from an ATG start codon or CTG start codon at position 10-12 of any of the nucleotide sequences of SEQ ID NOS: 5-8 of AAV8, AAV1, AAV6 and AAV9, respectively, or
      (ii) of serotype AAV8, said VP1.5 protein having the sequence of SEQ ID NO:3 or SEQ ID NO:4, and b) a viral vector genome, said genome comprising a minigene comprising AAV inverted terminal repeats and a heterologous nucleic acid sequence operably linked to regulatory sequences which direct expression of a product from the heterologous nucleic acid sequence in a host cell, wherein said rAAV vector capsid proteins package said viral vector genome and wherein said rAAV vector capsid proteins VP1, VP2, VP3, and VP1.5 are of the same serotype.

2. The AAV vector of claim 1 having a capsid serotype selected from the group consisting of AAV1, AAV8 and AAV9.

3. The AAV vector of claim 2, comprising VP1, VP2, VP3 and VP1.5, said VP 1.5 protein having the sequence of SEQ ID NO:3 or SEQ ID NO:4, wherein the amino acid at the amino terminus is either a leucine or a methionine.

4. The AAV vector of claim 2, which is AAV8.

5. The AAV vector according to claim 1 wherein the expression product of the heterologous nucleic acid sequence is therapeutic peptide.

6. The AAV vector according to claim 5, wherein the therapeutic peptide is a coagulation factor selection from the group consisting of an anti-viral RNAi molecule, Factor VIII, Factor IX or a functional fragment thereof.

7. The vector of claim 1 which is an AAV8 vector, wherein the expression product of the heterologous nucleic acid sequence is an IgG, IgM, IgA, IgD, IgE, chimeric immunoglobulin, humanized antibody, or a single chain antibody.

8. The AAV8 vector according to claim 4, wherein the expression product of the heterologous nucleic acid sequence is a chimeric immunoglobulin.

9. The AAV8 vector according to claim 4, wherein the expression product of the heterologous nucleic acid sequence is a single chain antibody.

10. The AAV vector of claim 5 wherein the expression product is an antiviral RNAi.

11. The AAV vector of claim 10, wherein said inhibitory RNA is effective to inhibit HCV infection and replication.

12. A pharmaceutical composition comprising the AAV vector according to claim 1 and a physiological compatible carrier therefor.

13. A cell culture comprising the vector according to claim 1.

14. A method of delivering a transgene to a cell in a subject, said method comprising the step of contacting the cell with the AAV vector according to claim 1 wherein said AAV vector comprises the transgene, wherein the presence of vp1.5 in said vector is associated with a reduced anti-capsid IgG response.

15. The method of claim 14, wherein said transgene is Factor IX.

16. The AAV vector of claim 1, wherein said VP1.5 protein comprises AAV1 VP 1.5 protein.

17. The AAV vector of claim 1, wherein said VP1.5 protein comprises AAV6 VP 1.5 protein.

18. The AAV vector of claim 1, wherein said VP1.5 protein comprises AAV8 VP 1.5 protein.

19. The AAV vector of claim 1, wherein said VP1.5 protein comprises AAV9 VP 1.5 protein.

20. A pharmaceutical composition comprising the AAV vector according to claim 16 and a physiological compatible carrier therefor.

21. A pharmaceutical composition comprising the AAV vector according to claim 17 and a physiological compatible carrier therefor.

22. A pharmaceutical composition comprising the AAV vector according to claim 19 and a physiological compatible carrier therefor.

* * * * *